US010299501B2

(12) United States Patent
Tan et al.

(10) Patent No.: US 10,299,501 B2
(45) Date of Patent: *May 28, 2019

(54) STABILIZER COMPOSITION OF MICROCRYSTALLINE CELLULOSE AND CARBOXYMETHYLCELLULOSE, METHOD FOR MAKING, AND USES

(71) Applicant: DUPONT NUTRITION USA, INC., Wilmington, DE (US)

(72) Inventors: Zheng Tan, Ewing, NJ (US); Maurice Gerard Lynch, Waterloo (BE); Michael Sestrick, Yardley, PA (US); Nadia Yaranossian, Brussels (BE)

(73) Assignee: DuPont Nutrition USA, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/789,411

(22) Filed: Oct. 20, 2017

(65) Prior Publication Data
US 2018/0042283 A1 Feb. 15, 2018

Related U.S. Application Data

(62) Division of application No. 14/349,186, filed as application No. PCT/US2012/000477 on Oct. 4, 2012, now Pat. No. 9,826,763.

(60) Provisional application No. 61/543,669, filed on Oct. 5, 2011.

(51) Int. Cl.
*A23L 29/206* (2016.01)
*A23C 9/154* (2006.01)
*C08L 1/04* (2006.01)
*C08L 1/28* (2006.01)
*A61K 8/73* (2006.01)
*A61Q 19/00* (2006.01)
*B01F 17/00* (2006.01)
*A23P 30/20* (2016.01)
*A23L 29/262* (2016.01)
*A23L 19/00* (2016.01)

(52) U.S. Cl.
CPC .......... *A23L 29/206* (2016.08); *A23C 9/1544* (2013.01); *A23L 19/09* (2016.08); *A23L 29/262* (2016.08); *A23P 30/20* (2016.08); *A61K 8/731* (2013.01); *A61Q 19/00* (2013.01); *B01F 17/0092* (2013.01); *C08L 1/04* (2013.01); *C08L 1/286* (2013.01); *A61K 2800/10* (2013.01); *A61K 2800/52* (2013.01)

(58) Field of Classification Search
CPC ... A23L 29/262; A23P 30/20; A61K 2800/52; A61K 8/731; B01F 17/0092
See application file for complete search history.

(56) References Cited

U.S. PATENT DOCUMENTS

| | | |
|---|---|---|
| 2,978,446 A | 4/1961 | Battista et al. |
| 3,023,104 A | 2/1962 | Battista et al. |
| 3,145,146 A | 8/1964 | Liberman et al. |
| 3,146,168 A | 8/1964 | Battista et al. |
| 3,539,365 A | 11/1970 | Durand et al. |
| 3,573,058 A | 3/1971 | Tiemstra |
| 3,639,169 A | 2/1972 | Broeg et al. |
| 4,017,598 A | 4/1977 | Ohno et al. |
| 4,110,476 A | 8/1978 | Rhodes |
| 4,263,334 A | 4/1981 | McGinley |
| 4,264,637 A | 4/1981 | Braverman |
| 4,311,717 A | 1/1982 | McGinley |
| 4,415,599 A | 11/1983 | Bos |
| 4,426,518 A | 1/1984 | Omiya |
| 4,693,750 A | 9/1987 | Bauer et al. |
| 4,725,441 A | 2/1988 | Porter |
| 4,744,987 A | 5/1988 | Mehra |
| 4,980,193 A | 12/1990 | Tuason, Jr. et al. |
| 5,082,684 A | 1/1992 | Fung |
| 5,192,569 A | 3/1993 | McGinley et al. |
| 5,272,137 A | 12/1993 | Blase |
| 5,286,510 A | 2/1994 | Bauer et al. |
| 5,366,724 A | 11/1994 | Pierre et al. |
| 5,366,742 A | 11/1994 | Tuason |
| 5,409,907 A | 4/1995 | Blase et al. |
| 5,415,804 A | 5/1995 | Minami |
| 5,505,982 A | 4/1996 | Krawczyk et al. |
| 5,543,511 A | 8/1996 | Bergfeld et al. |
| 5,573,777 A | 11/1996 | Serpelloni et al. |
| 5,605,712 A | 2/1997 | Bertrand et al. |
| 5,607,716 A | 3/1997 | Doherty et al. |
| 5,609,898 A | 3/1997 | Kaji et al. |
| 5,709,896 A | 1/1998 | Hartigan et al. |
| 5,725,886 A | 3/1998 | Erkoboni et al. |

(Continued)

FOREIGN PATENT DOCUMENTS

| EP | 1226818 A1 | 7/2002 |
|---|---|---|
| EP | 1681048 A1 | 7/2006 |

(Continued)

OTHER PUBLICATIONS

Sigma Product Information of Carboxymethylcellulose Sodium Salt (Published Aug. 2003).

(Continued)

*Primary Examiner* — Andrew S Rosenthal

(57) ABSTRACT

The subject matter of this invention is a composition and method of making a water-dispersible, stabilizing colloidal microcrystalline cellulose:carboxymethylcellulose composition. The method of making the composition does not require a salt solution as an anti-slip agent.

4 Claims, No Drawings

(56) References Cited

U.S. PATENT DOCUMENTS

| | | |
|---|---|---|
| 5,747,067 A | 5/1998 | Augello et al. |
| 5,769,934 A | 6/1998 | Ha et al. |
| 5,789,004 A | 8/1998 | Hogan et al. |
| 5,866,166 A | 2/1999 | Staniforth et al. |
| 6,010,734 A | 1/2000 | Whelan et al. |
| 6,025,007 A | 2/2000 | Krawczyk |
| 6,037,380 A | 3/2000 | Venables et al. |
| 6,079,630 A | 6/2000 | Schroeder |
| 6,106,865 A | 8/2000 | Staniforth et al. |
| 6,117,474 A | 9/2000 | Kamada et al. |
| 6,235,947 B1 | 5/2001 | Yoshinari et al. |
| 6,264,981 B1 | 7/2001 | Zhang et al. |
| 6,270,830 B1 | 8/2001 | Kamada et al. |
| 6,368,649 B1 | 4/2002 | van Bommel |
| 6,372,782 B1 | 4/2002 | Patel et al. |
| 6,391,368 B1 | 5/2002 | Tuason et al. |
| 6,432,448 B1 | 8/2002 | Augello et al. |
| 6,440,474 B1 | 8/2002 | Buliga et al. |
| 6,475,539 B1 | 11/2002 | Dewille et al. |
| 6,500,462 B1 | 12/2002 | Augello et al. |
| 6,503,918 B2 | 1/2003 | Yoshinari et al. |
| 6,517,871 B1 | 2/2003 | Vankatesh et al. |
| 6,548,093 B1 | 4/2003 | Collinge et al. |
| 6,689,405 B1 | 2/2004 | Tuason et al. |
| 6,709,713 B2 | 3/2004 | Augello et al. |
| 6,723,342 B1 | 4/2004 | Augello et al. |
| 6,726,949 B2 | 4/2004 | Adolphi et al. |
| 6,752,939 B2 | 6/2004 | Gereg |
| 6,753,017 B2 | 6/2004 | Berkulin et al. |
| 6,936,277 B2 | 8/2005 | Staniforth et al. |
| 6,936,628 B2 | 8/2005 | Lee |
| 7,462,232 B2 | 12/2008 | Tuason et al. |
| 7,625,622 B2 | 12/2009 | Teckoe et al. |
| 7,785,089 B2 | 12/2010 | Teckoe et al. |
| 7,879,382 B2 | 2/2011 | Tuason et al. |
| 2003/0017204 A1 | 1/2003 | Augello et al. |
| 2003/0129238 A1 | 7/2003 | Augello et al. |
| 2004/0071821 A1 | 4/2004 | Ashourian et al. |
| 2004/0121006 A1 | 6/2004 | Narita et al. |
| 2004/0137043 A1 | 7/2004 | Augello et al. |
| 2004/0185161 A1 | 9/2004 | Ashourian et al. |
| 2005/0147710 A1 | 7/2005 | Teckoe et al. |
| 2005/0220824 A1 | 10/2005 | Kessel et al. |
| 2005/0233046 A1 | 10/2005 | Krawczyk et al. |
| 2005/0233053 A1 | 10/2005 | Shen et al. |
| 2005/0258827 A1 | 11/2005 | Patland et al. |
| 2005/0266116 A1 | 12/2005 | Teckoe et al. |
| 2006/0127451 A1 | 6/2006 | Augello et al. |
| 2007/0128333 A1 | 6/2007 | Tuason et al. |
| 2008/0131543 A1 | 6/2008 | Li et al. |
| 2008/0213360 A1 | 9/2008 | Thoorens et al. |
| 2009/0110799 A1 | 4/2009 | Funami et al. |
| 2009/0130287 A1 | 5/2009 | Tuason et al. |
| 2011/0143009 A1* | 6/2011 | Tuason ............... A23C 9/1542 426/572 |
| 2011/0151097 A1 | 6/2011 | Tuason et al. |
| 2013/0064953 A1* | 3/2013 | Bache ................ A23C 9/1544 426/573 |

FOREIGN PATENT DOCUMENTS

| | | |
|---|---|---|
| GB | 1010477 | 11/1965 |
| GB | 1567049 | 5/1980 |
| GB | 2395413 A | 5/2004 |
| JP | 08151481 A | 6/1996 |
| JP | 9266779 | 10/1997 |
| JP | 10-056960 | 3/1998 |
| JP | 10237220 A | 9/1998 |
| JP | 11046723 A | 2/1999 |
| JP | 11299435 A | 11/1999 |
| JP | 2000-184853 | 7/2000 |
| JP | 2001190220 A | 7/2001 |
| JP | 2002125587 A | 5/2002 |
| JP | 2002345401 A2 | 12/2002 |
| JP | 2005-245217 | 12/2005 |
| SU | 467105 | 12/1975 |
| WO | 8102521 A1 | 9/1981 |
| WO | 92/01390 | 2/1992 |
| WO | 9424888 A1 | 11/1994 |
| WO | 9856826 A1 | 12/1998 |
| WO | 0119348 A1 | 3/2001 |
| WO | 0132150 | 5/2001 |
| WO | 0132152 | 5/2001 |
| WO | 0249451 A2 | 6/2002 |
| WO | 03003843 A1 | 1/2003 |
| WO | 03090558 A1 | 11/2003 |
| WO | 03096976 A2 | 11/2003 |
| WO | 2005030177 A2 | 4/2005 |
| WO | 2005096832 A2 | 10/2005 |
| WO | 0004862 A2 | 12/2005 |
| WO | 200631963 A1 | 12/2006 |

OTHER PUBLICATIONS

Bowman, B.J. Ph.D. et al., "Colloidal Dispersions", Chapter 21 of Remington: The Science and Practice of Pharmacy, 21st Edition, 2005, Lippincott Williams and Wilkins. Philadelphia, Pa.

Mitchell, S.A., et al. "A Compaction Process to enhance dissolution of poorly water-soluble drugs using hydroxypropyl methylcellulose". International Journal of Pharmaceutics, 20, pp. 3-11, 2003.

Keinebudde, P., "Roll Compaction/Dry Granulation: Pharmaceutical Applications". European Journal of Pharmaceutics and biopharmaceutics, 58, pp. 317-326, 2004.

Deyampertrogers, Tracey L., "Contest Considerations for Low Dosage Drug Formulations Processed by Roller compaction", Ph.D. Thesis, Purdue University, Aug. 1997.

Deyampert Rogers, Tracey L, "Oral Preliminary Examination", Sep. 1, 1995.

Falzone, Angela Marie, "Roller Compaction of Pharmaceutical Excipients and Excipient-drug Blends", Ph.D. Thesis, Purdue Univeristy, Dec. 1990.

Skinner, G.W., "The Evaluation of Fine-particle Hydroxyprpycellulose as a Roller Compaction binder in Pharmaceutical Applications". Drug Development & Indust. Pharm, 25(10), pp. 1121-1128, 1999.

The Fitzpatrick Company Europe N.V., "Introduction to Roll Compcation and the Fitzpatrick Chilsonator" Mar. 1997.

Sheskey, P. et al. "Roll Compaction Granulation of a Controlled-Release Matrix Tablet Formulation Containing HPMC", Pharmaceutical Technology, Oct. 1999.

Zhang, Y. et al. "Physical Properties and Compact Analysis of Commonly Used Direct Compression Binders", AAPS Pharm. Sci. Tech. 4(4) Article 62, Dec. 15, 2003.

Hisiu-o, H. et al., "Characteristics of Codried Products of Microcrysalline Cellulose with Saccharides and Low-substituted Hydroxyproplycellulose", Powder Technology, 127, 2002, pp. 45-53.

Gohel, M.C., "A Review of co-processed Directly Compressible Excipients", Journal of Pharma, Pharma. Sci. 8(1), pp. 76-93, 2005.

Schroder, R. et al., Influence of Magnesium Stearate on the Compaction Behavior and Tablet characteristics of Co-Spray Dried Compounds vs. Physical Blends. Poster Presented at American Association of Pharmaceutical Science (Denver) Oct. 2001.

Jacobs S. et al. "Novel Co-processed Excipients of Mannitol and Microcrystalline Cellulose for Preparing Fast Dissolving tablets of Glipzide", Indian Journal of Pharmaceutical Sciences, vol. 69, (5) Sep.-Oct. 2007, pp. 633-639.

Rowe, Sheskey & Weller, "Handbook of Pharmacuetical Excipients, Fourth Edition", 2003, Pharmaceutical Press, London. XP002281910, p. 110, col. 2.

* cited by examiner

STABILIZER COMPOSITION OF MICROCRYSTALLINE CELLULOSE AND CARBOXYMETHYLCELLULOSE, METHOD FOR MAKING, AND USES

CROSS-REFERENCE

This application is a divisional application of U.S. application Ser. No. 14/349,186 filed on Apr. 2, 2014 a 371 National filing from International Application Number PCT/US12/00477, filed on Oct. 4, 2012 and which claims the benefit of U.S. Provisional Application No. 61/543,669 filed on Oct. 5, 2011, the disclosure of each of which are incorporated herein by reference in its entirety.

FIELD OF THE INVENTION

The invention relates to a microcrystalline cellulose:carboxymethyl cellulose composition for use as a stabilizer and dispersant in aqueous media, as well as to methods of manufacture thereof.

BACKGROUND OF THE INVENTION

Microcrystalline cellulose, also known as MCC or cellulose gel, is commonly used in the food industry to enhance the properties or attributes of a final food product. For example, it has been used as a binder and stabilizer in food applications, including in beverages, and as stabilizers. It has also been used as a binder and disintegrant in pharmaceutical tablets, as a suspending agent in liquid pharmaceutical formulations, and as binders, disintegrants, and processing aids in industrial applications, in household products such as detergent and/or bleach tablets, in agricultural formulations, and in personal care products such as dentifrices and cosmetics.

Microcrystalline cellulose is produced by treating a source of cellulose, preferably alpha cellulose in the form of pulp from fibrous plant materials, with a mineral acid, preferably hydrochloric acid (acid hydrolysis). The acid selectively attacks the less ordered regions of the cellulose polymer chain thereby exposing and freeing the crystalline sites which form crystallite aggregates which constitute the microcrystalline cellulose. These are then separated from the reaction mixture, and washed to remove degraded by-products. The resulting wet mass, generally containing 40 to 60 percent moisture, is referred to in the art by several names, including 'hydrolyzed cellulose', 'hydrolyzed cellulose wetcake', 'level-off DP cellulose', 'microcrystalline cellulose wetcake', or simply 'wetcake'.

The classic process for MCC production is acid hydrolysis of purified cellulose, pioneered by O. A. Battista (U.S. Pat. Nos. 2,978,446; 3,023,104; and 3,146,168). In efforts to reduce the cost while maintaining or improving the quality of MCC, various alternative processes have been proposed. Among these are steam explosion (U.S. Pat. No. 5,769,934; Ha et al.), reactive extrusion (U.S. Pat. No. 6,228,213; Hanna et al.), one-step hydrolysis and bleaching (World Patent Publication WO 01/0244; Schaible et al.), and partial hydrolysis of a semi-crystalline cellulose and water reaction liquor in a reactor pressurized with oxygen and/or carbon dioxide gas and operating at 100 to 200° C. (U.S. Pat. No. 5,543,511; Bergfeld et al.).

Microcrystalline cellulose and/or hydrolyzed cellulose wetcake has been modified for a variety of uses. In food products it is used as a gelling agent, a thickener a fat substitute and/or non-caloric filler, and as a suspension stabilizer and/or texturizer. It has also been used as an emulsion stabilizer and suspending agent in pharmaceutical and cosmetic lotions and creams. Modification for such uses is carried out by subjecting micro-crystalline cellulose or wetcake to intense attrition (high shear) forces as a result of which the crystallites are substantially subdivided to produce finely divided particles. However, as particle size is diminished, the individual particles tend to agglomerate or horrify upon drying. A protective colloid (such as sodium carboxy-methylcellulose (CMC)) may be added during attrition or following attrition but before drying. The protective colloid wholly or partially neutralizes the hydrogen or other bonding forces between the smaller sized particles. Colloidal microcrystalline cellulose, such as the carboxymethyl cellulose-coated microcrystalline cellulose described in U.S. Pat. No. 3,539,365 (Durand et al.). This additive also facilitates re-dispersion of the material following drying. The resulting material is frequently referred to as attrited microcrystalline cellulose or colloidal microcrystalline cellulose.

On being dispersed in water, colloidal microcrystalline cellulose forms white, opaque, thixotropic gels with microcrystalline cellulose particles less than 1 micron in size. FMC Corporation (Philadelphia, Pa., USA) manufactures and sells various grades of this product which comprise co-processed microcrystalline cellulose and sodium carboxymethylcellulose under the designations of, among others, AVICEL® and GELSTAR®.

There remains a need, however, to obtain a colloidal microcrystalline cellulose composition having enhanced gel strength, enhanced stabilization, and other desirable rheological properties useful to a variety of applications, particularly food products.

SUMMARY OF THE INVENTION

The invention encompasses a process for making a stabilizer composition comprising:
 a) blending a microcrystalline cellulose wetcake with a first carboxymethyl cellulose having a DS of 0.45-0.85 in an amount of 5% to 25% by weight of the total composition;
 b) extruding the product of step a);
 c) either
  i) blending and subsequently extruding a second carboxymethylcellulose having a DS of 0.9-1.5 in an amount of 2% to 20% by weight of the total composition, into the product of step b), or
  ii) preparing a water dispersion comprising the microcrystalline cellulose:carboxymethyl cellulose extrudate of step b) and a second carboxymethyl cellulose having a DS of 0.9-1.5 wherein the second carboxymethyl cellulose having a DS of 0.9-1.5 is present in an amount of 2% to 20% by weight of the total composition; and
 d) drying the product of step c).

The second carboxymethyl cellulose of step c) is preferably in an amount of 4% to 8% by weight of the total composition. The first carboxymethyl cellulose is preferably sodium carboxymethyl cellulose having a DS of about 0.7 and the second carboxymethyl cellulose is preferably sodium carboxymethyl cellulose having a DS of about 1.2. The drying step may be by spray drying, fluidized bed drying, flash drying, or bulk drying.

Further embodiments encompass a food product comprising the stabilizer composition produced by the disclosed methods. A further embodiment encompasses an industrial suspension comprising the stabilizer composition adapted for use in pharmaceutical products, nutraceutical products, healthcare products, cosmetic products, personal care products, consumer products, agricultural products, or chemical formulations.

An additional embodiment of the invention is a stabilizer composition comprising microcrystalline cellulose and a mixture of a first carboxymethyl cellulose having a DS of 0.45-0.85 in an amount of 5% to 25% by weight of the total composition and a second carboxymethyl cellulose having a DS of 0.9-1.5 in an amount of 2%-20% by weight of the total composition, wherein the stabilizer composition has an initial viscosity of at least 750 cps, a set-up viscosity of at least 3200 cps, and a set-up gel strength G' of at least 20 Pa when dispersed in water at 2.6% solids concentration.

A further embodiment of the present invention is a stabilizer composition comprising a) microcrystalline cellulose and b) a mixture of i) a first carboxymethyl cellulose having a DS of 0.45-0.85 in an amount of 5%-25% by weight of the composition, and ii) a second carboxymethyl cellulose having a DS of 0.9-1.0, wherein the composition is made by the following sequential process steps: 1) co-extruding a microcrystalline cellulose wetcake with a first carboxymethyl cellulose having a DS of 0.45-0.85 for sufficient attrition and interaction; 2) either i) blending a second carboxymethyl cellulose having a DS of 0.9-1.0 into the product of step 1 followed by extruding; or ii) preparing a water dispersion comprising the microcrystalline cellulose:carboxymethyl cellulose extrudate of step 1 and a second carboxymethyl cellulose having a DS of 0.9-1.0; and 3) drying the product of step 2.

A still further embodiment of the present invention is a stabilizer composition comprising a) microcrystalline cellulose b) a carboxymethyl cellulose having a DS of 0.45-0.85 in an amount of 5%-25% by weight of the composition, and c) at least one additional hydrocolloid in an amount of 5%-50% by weight of the composition, wherein the composition is made by the following sequential process steps: i) co-extruding a microcrystalline cellulose wetcake with a carboxymethyl cellulose having a DS of 0.45-0.85 in an amount of 5%-25% by weight of the composition for sufficient attrition and interaction; ii) either (a) preparing a water dispersion comprising the microcrystalline cellulose:carboxymethyl cellulose extrudate of step i and at least one additional hydrocolloid; or (b) blending in at least one additional hydrocolloid to the product of step i., then extruding the admixture; and iii) drying the product of step ii).

Other features and advantages of the foregoing embodiments will be apparent from the following detailed description and from the claims. The disclosed embodiments are exemplary and explanatory only and not to be considered to be restrictive of the invention.

DETAILED DESCRIPTION OF THE PREFERRED EMBODIMENTS

The present invention encompasses a colloidal microcrystalline cellulose made with carboxymethylcelluloses of low and high degrees of substitution (DS) and without a salt solution attriting aid. The resulting product is useful as a stabilizer in edible food products. Additionally, the present invention encompasses a process to overcome direct extrusion processing challenges of MCC wetcake admixed with a high DS CMC.

The present inventive method permits the use of CMC having a high DS or of other "slippery" hydrocolloids to make high performing colloidal MCC. In one embodiment, MCC wetcake is extruded with a low DS CMC, followed by extrusion (or dispersing and blending in) of the first extrudate with a high DS CMC or other "slippery" hydrocolloid. Salt is not required as an attriting agent in this method.

In one embodiment, sufficient extrusion/attrition may be achieved in two or more steps. For instance, the MCC wetcake and low DS CMC is extruded/attrited first and then followed by a high DS CMC addition and extrusion/attrition.

The inventors believe, without being bound to the theory, that by first extruding and coating the MCC wetcake particles with a first CMC having a low DS to effect significant MCC/CMC interaction, a second CMC having a high DS (and otherwise too 'slippery' to be directly incorporated effectively into the extrusion composition) can then coat and bond with the first CMC low DS surfaces immobilized on the MCC:CMC particles, as well as coat the remaining MCC surfaces The spray dried product powder thus made, will have superior dispersion properties even at very low shear application conditions.

"Colloid" and "colloidal" are used interchangeably in the specification to define particles that may be suspended in a mixture. As known to those of ordinary skill in the art, colloidal particles are of a certain average particle size, for example, on the order of about 0.1 to 10 microns. The colloidal particles described herein may be of any suitable particles size, provided that they are able to form colloidal suspensions.

"Gel" refers to a soft, solid, or solid-like material which consists of at least two components, one of which is a liquid present in abundance (Almdal, K., Dyre, J., Hvidt, S., Kramer, O.; Towards a phenomenological definition of the term 'gel'. *Polymer and Gel Networks* 1993, 1, 5-17).

"Gel strength G'" refers to the reversibly stored energy of the system (the elastic modulus G') and relative to the compositions herein is a function of the cellulose concentration. The measurement is made with a TA-Instruments rheometer (ARES-RFS3) with oscillatory strain sweep at 1 Hz and at 20° C., with gap size at 1.8 mm Testing is performed at 24 hours set up of a 2.6% solids dispersion of the composition in deionized water.

The Brookfield viscosity test is used to obtain an initial viscosity on the activated compositions (2.6% solids dispersion of the material in deionized water) and repeated to obtain viscosity after 24 hours. A RVT viscometer, with an appropriate spindle, is used at 20 rpm, at 20° to 23° C.

Microcrystalline Cellulose Wetcake:

Microcrystalline cellulose wetcake from any source may be employed in the methods. Suitable feedstocks from which MCC may be obtained include, for example, wood pulp [such as bleached sulfite and sulfate pulps], corn husks, bagasse, straw, cotton, cotton linters, flax, hemp, ramie, seaweed, cellulose, and fermented cellulose. Additional feedstocks include bleached softwood kraft pulps, bleached hardwood kraft pulps, bleached Eucalyptus kraft pulps, paper pulps, fluff pulps, dissolving pulps, and bleached non-wood cellulosic pulps. In one embodiment, the MCC used is one approved for human consumption by the United States Food and Drug Administration.

Carboxymethylcellulose:

The carboxymethylcellulose used is preferably alkali metal carboxymethylcellulose, for instance, sodium, potassium, or ammonium CMC. Most preferably, the carboxymethyl cellulose is sodium CMC.

The CMC is characterized by, inter alia, the degree of substitution (DS) that is present. The degree of substitution represents the average number of hydroxyl groups substituted per anhydroglucose unit. For example, in CMC, each anhydroglucose unit contains three hydroxyl groups, which gives CMC a maximum theoretical DS of 3.0. Two commercially available carboxymethylcelluloses are AQUALON®7LF (low viscosity) and AQUALON®7MF (medium viscosity), both with a DS of 0.7, which is an average of 7 carboxymethyl groups per 10 anhydroglucose units (Ashland, Inc., Wilmington, Del., USA). A high DS, medium viscosity CMC is 12M8F (Ashland). Another high DS, medium viscosity CMC is 12M31P (Ashland). A high DS, high viscosity CMC is 9H7F CMC (Ashland). An additional CMC is DrisPac CMC (Ashland)

The present invention uses carboxymethylcelluloses having two ranges of degree of substitution. The first carboxymethylcellulose has a degree of substitution of about 0.45 to about 0.85. In some embodiments, the first carboxymethylcellulose has a degree of substitution of 0.45 to 0.80. In still other embodiments, the first carboxymethylcellulose has a degree of substitution of about 0.7. The second carboxymethylcellulose has a degree of substitution of 0.9 to 1.5. Still, in other embodiments, the second carboxymethylcellulose has a degree of substitution of 0.9 to 1.2. The first and second carboxymethylcelluloses contemplated for use in the present methods are respectively of low and high degrees of substitution and varying levels of viscosity.

The quantities of MCC and carboxymethylcellulose incorporated into these compositions are such that the weight ratio of MCC:carboxymethylcellulose is about 50:50 to about 95:5, respectively. Preferred is a weight ratio of MCC:CMC ranging from about 95:5 to about 70:30, respectively. The most preferred weight ratio is 85:15.

Also disclosed are methods for forming the compositions provided herein. The methods include mixing a first water-soluble carboxymethylcellulose having a low DS with microcrystalline cellulose wetcake, wherein the weight ratio of the microcrystalline cellulose to the carboxymethylcellulose is about 50:50 to about 95:5. The moist mixture is extruded to effect intimate mixing among the components. A second water-soluble carboxymethylcellulose having a high DS is blended into the colloidal MCC:CMC extrudate.

As used in this specification, the terms "attrited" and "attrition" are used interchangeably to mean a process that effectively reduces the size of at least some if not all of the particles to a colloidal size. The processing is a mechanical processing that introduces shearing force either to an MCC wetcake before blending with CMC or to an admixture of MCC wetcake and CMC. "Co-attrition" is used to refer to applications of high shear forces to an admixture of the MCC and CMC component. Suitable attrition conditions may be obtained, for example, by co-extruding, milling, or kneading. The extrudent can be dried or be dispersed in water to form a slurry. In addition to various types of extruders as practiced in current MCC manufacturing, other examples of equipment for attriting wetcake or MCC:CMC include compression rolls/belts, calendaring rolls, mechanical refiner discs, ultrasonic refiners, high pressure homogenizers (including Micro-fluidic devices), high compression planetary mixers, and shockwave/cavitation devices.

Extruded colloidal MCC:CMC is dispersed in water to form a slurry. The slurry can be homogenized and spray dried. Dry particles formed from the spray drying can be reconstituted in a desired aqueous medium or solution to form the compositions, edible food products, and industrial application suspensions described herein. The extruded mixture can be dried by processes other than spray drying, such as, for example, fluidized bed drying, drum drying, bulk drying, and flash drying.

Other features and advantages of the foregoing embodiments will be apparent from the following detailed description and from the claims. The foregoing general description and detailed description of certain embodiments are exemplary and explanatory only and are not to be considered to be restrictive of the invention.

Applications:

Further, edible food products are disclosed that are formed from the present compositions. These food products may include emulsions, beverages, films, sauces, soups, dressings, dairy and non-dairy milks and products, frozen desserts, and cultured foods. The edible food products can additionally comprise diverse edible material and additives, including proteins, fruit juices, vegetable juices, fruit-flavored substances, or any combination thereof. In addition, a number of non-food suspensions are disclosed that comprise the present compositions that are adapted for use in a pharmaceutical, nutraceutrical, cosmetic, personal care product, agriculture product, or chemical formulation.

The described compositions can act as stabilizers that have a multitude of industrial and consumer uses. These applications are in the food and beverage industry or in suspensions for pharmaceutical, health care, and other industrial applications. The compositions, after drying to powder form, can be mixed with an aqueous solution to form a colloidal mix. In some embodiments, the compositions maintain their colloidal properties for greater periods of time and under more harsh conditions than previously known compositions. Some of the edible food products formed using the compositions described herein provide stable colloidal properties for extended periods even at acidic pH conditions. Some examples of the edible food products include the following: sauces (especially low pH/high salt types), retorted soups, dressings including both spoonable and pourable dressings, beverages including those that are heat treated, for example, by pasteurization or ultra pasteurization, or heat treated using ultra high temperature (UHT) or high temperature short time (HTST) or retort processes, UHT and retort processed protein and nutritional beverages, UHT processed low pH protein-based beverages, UHT Ca fortified beverages, UHT milk-based beverages, UHT and retort processed milk creams, low pH frozen desserts (e.g., fruit sherbets), aerated food systems dairy and non-dairy based, cultured products (sour cream, yogurts), and bakery fillings or creams. The colloidal MCC:CMC composition in bakery fillings provides excellent stability of the filling during oven baking. The levels of the compositions used in the contemplated food products can range from about 0.05% to about 3.5% by weight of total food product, and in some instances 0.2% to 2% by weight of total food product. In some of these edible food products, an adjunct stabilizer can be added to assist in long term stability (e.g., additional CMC can be added in the amounts of about 0.05% to about 0.5%).

In some embodiments, edible food products are provided that include the present compositions. These food products can also include other edible ingredients such as, for example, vegetable or fruit pulps, mineral salts, protein sources, fruit juices, acidulants, sweeteners, buffering agents, pH modifiers, stabilizing salts, or a combination thereof. Those skilled in the art will recognize that any number of other edible components may also be added, for example, additional flavorings, colorings, preservatives, pH buffers, nutritional supplements, process aids, and the like. The additional edible ingredients can be soluble or insoluble, and, if insoluble, can be suspended in the food product. In some of the edible food products, the compositions are generally comprised of stabilizer, protein, and/or fruit juice (e.g., fruit juices containing solids (such as pulp) and nectars are readily stabilized by adding the stabilizer compositions). In such blends having only juice or only protein, the composition of the stabilizer composition and the amount of stabilizer composition used in the beverage blend may need to be adjusted accordingly to maintain the desired stability results. Such routine adjustment of the composition is fully within the capabilities of one having skill in the art and is within the scope and intent of the present invention. These edible food products can be dry mix products (instant sauces, gravies, soups, instant cocoa drinks, etc.), low pH dairy systems (sour cream/yogurt, yogurt drinks, stabilized frozen yogurt, etc.), baked goods, and as a bulking agent in non-aqueous food systems and in low moisture food systems.

Suitable juices incorporating the stabilizer composition include fruit juices (including but not limited to lemon juice, lime juice, and orange juice, including variations such as lemonade, limeade, or orangeade, white and red grape juices, grapefruit juice, apple juice, pear juice, cranberry juice, blueberry juice, raspberry juice, cherry juice, pineapple juice, pomegranate juice, mango juice, apricot juice or nectar, strawberry juice, and kiwi juice) and vegetable juices (including but not limited to tomato juice, carrot juice, celery juice, beet juice, parsley juice, spinach juice, and lettuce juice). The juices may be in any form, including liquid, solid, or semi-solid forms such as gels or other concentrates, ices or sorbets, or powders, and may also contain suspended solids. In another embodiment, fruit-flavored or other sweetened substances, including naturally flavored, artificially flavored, or those with other natural flavors ("WONF"), may be used instead of fruit juice. Such fruit flavored substances may also be in the form of liquids, solids, or semi-solids, such as powders, gels or other concentrates, ices, or sorbets, and may also contain suspended solids.

Proteins suitable for the edible food products incorporating the stabilizer compositions include food proteins and amino acids, which can be beneficial to mammals, birds, reptiles, and fish. Food proteins include animal or plant proteins and fractions or derivatives thereof. Animal derived proteins include milk and milk derived products, such as heavy cream, light cream, whole milk, low fat milk, skim milk, fortified milk including protein fortified milk, processed milk and milk products including superheated and/or condensed, sweetened or unsweetened skin milk or whole milk, dried milk powders including whole milk powder and nonfat dry milk (NFDM), casein and caseinates, whey and whey derived products such as whey concentrate, delactosed whey, demineralized whey, whey protein isolate. Egg and egg-derived proteins may also be used. Plant derived proteins include nut and nut derived proteins, sorghum, legume and legume derived proteins such as soy and soy derived products such as untreated fresh soy, fluid soy, soy concentrate, soy isolate, soy flour, and rice proteins, and all forms and fractions thereof. Food proteins may be used in any available form, including liquid, condensed, or powdered. When using a powdered protein source, however, it may be desirable to prehydrate the protein source prior to blending with stabilizer compositions and juice for added stability of the resulting beverage. When protein is added in conjunction with a fruit or vegetable juice, the amount used will depend upon the desired end result. Typical amounts of protein range from about 1 to about 20 grams per 8 oz. serving of the resulting stable edible food products, such as beverages, but may be higher depending upon the application.

Other products and applications for which the present compositions, or stabilizer compositions, may be used include industrial suspensions. In some embodiments, the industrial suspensions include the present compositions that are adapted for use in pharmaceuticals, cosmetics, personal care products, agricultural products, or chemical formulations. Some examples of industrial applications include excipients for chewable tablets, providing taste masking for drug actives (such as APAP, aspirin, ibuprofen, etc.); suspending agents; controlled release agents in pharmaceutical applications; delivery systems for flavoring agents and nutraceutical ingredients in food, pharmaceutical, and agricultural applications; direct compression sustained release agents, which can be used as pharmaceutical dosage forms such as tablets, films, and suspensions; thickeners, which can be used in foams, creams, and lotions for personal care applications; suspending agents, which can be used with pigments and fillers in ceramics, colorants, cosmetics, and oral care; materials such as ceramics; delivery systems for pesticides including insecticides; and other agricultural products.

In certain embodiments, the compositions, generally including microcrystalline cellulose and at least one water soluble carboxymethylcellulose, are formulated as dry blends. At least one of an additional hydrocolloid, a surfactant, an active substance, and a filler can be added to the dry blends. In preferred embodiments, as additional hydrocolloid is added to the dry blends. The dry blends are suitable intermediates that can be dosed and dispersed with sufficient water and agitation with heat as appropriate to activate the stabilizer in the desired food, pharmaceutical, industrial, or cosmetic product or application.

In alternative embodiments, at least one of an additional hydrocolloid, a surfactant, an active substance, and a filler is added to a slurry generally including microcrystalline cellulose, and at least one water soluble carboxymethylcellulose, and the slurry is then spray dried.

Suitable additional hydrocolloids can be any used in the food industry. These hydrocolloids include, but are not limited to, starches and modified starches, water-soluble and water-dispersible gums, polysaccharides, and synthetic polymers, such as, for example, pectins, including high methoxyl ("HM") and low methoxyl pectins and acetylated pectins [such as beet pectin], low degree-of-substitution carboxymethylcellulose ("CMC"), high degree-of-substitution ("high DS") carboxymethylcellulose ("CMC"), hydroxypropyl cellulose, hydroxypropyl methyl cellulose, alginate, karaya gum, xanthan gum, arabic gum, gellan gum, PGA, carrageenan, tragacanth, and galactomannans (such as guar gum, locust bean gum, tara gum, cassia gum), Konjac glucommanans, tamarind seed gum, and mixtures thereof. In some embodiments, the additional hydrocolloid is starch, xanthan gum, high DS CMC, or pectin. One example of a starch is a tapioca starch such as National Frigex HV (from National Starch Company). Tamarind seed gum based products can be used in low pH protein beverage applications. Examples include, low ph soy beverages, acidic milk juice, and fermented milk products.

The additional hydrocolloids can be employed in a number of ways. In certain embodiments, an additional hydrocolloid is added to the dry blend or to the slurry during production of the stabilizer compositions described herein. For example, the hydrocolloid is added to the slurry just prior to spray drying, so that the entire mixture is spray-dried at once. The resulting dry mixture of the stabilizer composition plus an additional hydrocolloid may then be packaged and stored, and added as a single measure during production of the food, pharmaceutical, industrial, or cosmetic products described herein.

In alternative embodiments, the additional hydrocolloid is added in a supplementary step at the time of production, in an amount suited to the particular product being manufactured.

The additional hydrocolloids are employed in amounts sufficient to enhance the stabilizing function of the MCC: carboxymethylcellulose compositions in the final food, pharmaceutical, industrial, or cosmetic product. For example, in a beverage, an adjunct stabilizer can be employed in a sufficient amount to reduce serum separation in the final beverage.

Suitable surfactants include, but are not limited to, ionic or nonionic with an HLB of 1 to 40. Active substances may be added to the compositions and include, but are not limited to, at least one of a nutraceutical agent, a vitamin, a mineral, a coloring agent, a sweetener, a flavorant, a fragrance, a salivary stimulant agent, a food, an oral care agent, a breath freshening agent, a pharmaceutical active, agricultural active, therapeutic agent, cosmetic agent, chemical, buffer, or pH modifier. Active substances can be encapsulated or otherwise processed or treated to modify their release properties.

The particular filler used depends upon its ability to modify the blend and/or the desired product. Insoluble fillers, such as pigments like titanium dioxide, and insoluble but swellable fillers, such as gel particles, celluloses or microcrystalline cellulose, form suspensions or dispersions with the activated stabilizer. Alternatively, fillers can be water-soluble and capable of readily dissolving in water, such as sugar or maltodextrin, or reactive, for example, pH sensitive or temperature sensitive and capable of dissolving under specific process conditions, such as calcium carbonate.

When manufacturing edible products or beverages having a low-pH phase and a protein phase it is also possible to achieve a desirable level of stability by manufacturing edible products or beverages in a single phase. In such a single-phase process, the stabilizer composition and optional additional hydrocolloid may be dispersed in water. Additional ingredients, including but not limited to proteins, fruit juices, acidulants, buffers, sweeteners, pH modifiers, antifoaming agents, and salts may then be added to the present compositions in a single phase. The order of addition of any additional ingredients should be selected to insure protein protection both during assembly of the edible product or beverage and thereafter.

Additional ingredients may be added to the edible compositions, or edible food products, disclosed herein. Such additional ingredients which may be desirable and can include, but are not limited to, pH modifiers such as acidulants (including citric, malic, tartaric, phosphoric, acetic, and lactic acids and the like), buffering agents (including carbonates, citrates, phosphates, sulfates, maleates, and the like), or the like that may be added to either the juice or protein components at any stage of production, sweeteners (such as sugar, corn syrup, fructose, etc), high intensity sweeteners (such as aspartame), sweetener alternatives (such as sucralose) or sugar alcohols (such as sorbitol, mannitol, and maltitol). In one embodiment, a sugar alternative such as sucralose, aspartame, or acesulfame K is used to produce a resulting composition that is low in carbohydrate content. Further possible additives include flavors, colorants, emulsifiers, preservatives, fillers such as maltodextrins, alcohol compositions, concentrates, and nutritional additives (such as calcium, i.e. calcium maleate or other minerals, vitamins, herbal supplements, etc.). Optional process aids such as an antifoam agent may also be used in these applications.

Many of the edible food products disclosed herein can benefit from the stabilizer compositions, which are the edible food products that include low pH liquids, wherein the resulting pH is greater than about 2.5 and less than about 7.0. In one embodiment, the pH of the food product is between about 2.8 and about 6.5. In a further embodiment, the pH of the food product is between about 3.0 and about 6.0. The pH can also be less than about 5.5. The compositions can be either alcoholic or non-alcoholic in nature.

The final beverage compositions may be processed by heat treatment in any number of ways. These methods may include, but are not limited to, pasteurization, ultra pasteurization, high temperature short time pasteurization ("HTST"), and ultra high temperature pasteurization ("UHT"). These beverage compositions may also be retort processed, either by rotary retort or static retort processing. Some compositions, such as juice-added or natural or artificially flavored soft drinks may also be cold processed. Many of these processes may also incorporate homogenization or other shearing methods. There may also be co-dried compositions, which can be prepared in dry-mix form, and then conveniently reconstituted for consumption as needed. The resulting beverage compositions may be refrigerated and stored for a commercially acceptable period of time. In the alternative, the resulting beverages may be stored at room temperature, provided they are filled under aseptic conditions.

In some embodiments, the disclosed edible food products have enhanced storage stability and, therefore, greater commercial appeal. Stable compositions are those that exhibit acceptable levels of storage stability. Storage stability is intended to mean at least one or more of the following product characteristics over the desired shelf life of the product: in liquid systems—suspension with minimal or no sedimentation, minimal or no serum separation, minimal or no creaming, minimal or no mottling, absence of rippling, absence of localized gels or gelation; in solid, semi-solid, gel, foam or film systems—minimal or no serum separation, deaeration or coalescence; and additionally for frozen systems—reduction or avoidance of the growth in size or number of ice crystals. As used in the foregoing description, minimal sedimentation means that any sediment that exists is present as loose sediment, which may be easily shaken back into the system. As used in the foregoing description, minimal serum separation means that less than 5 mm of serum is present when the liquid system is viewed in a 250 mL flask. In some embodiments, the edible food products can have enhanced storage ability without the need for adjunct stabilizers (outside of carboxymethylcelluloses used in compositions). For example, some sauces that lack an adjunct stabilizer, such as xanthan gum, are shown to maintain relative viscosity for extended periods of time, which in some instances is at least six months.

In order to describe the invention in more detail, the following non-limiting examples are set forth:

EXAMPLES

Comparative Material 1

Avicel®RC-591

AVICEL®RC-591 is a dispersible, colloidal MCC comprising medium viscosity, low DS CMC. It is manufactured by FMC Corporation, Philadelphia, Pa. It is used in food and pharmaceutical suspensions to regulate and modify viscosity and for its thixotropic characteristics. It is heat and freeze-thaw stable, has long shelf-life stability, is stable at pH range 4-11, and is odorless/tasteless.

When dispersed in deionized water, at 1.2% solids, it exhibited an initial Brookfield viscosity at room temperature of 40-175 cps, and a set-up viscosity after 24 hrs of 900 to 1600 cps. When the 1.2% solids dispersion was measured by a Texas Instruments Rheometer after 24 hrs set-up, it exhibited a gel strength G' of 23 Pa. When dispersed at 2.6% solids in water, the gel strength G' became 30 Pa.

Example 1

Co-Extruded MCC:CMC 7LF, then blended in 12M31P CMC

First, 85% MCC wetcake was co-extruded with 15% CMC 7LF (Ashland). Then the MCC:CMC7LF extrudate was dispersed in water and blended with 5% weight 12M31P CMC (Ashland) based on the total weight of MCC:CMC7LF. Thereafter, the blended system was homogenized and spray-dried into powder. The final powder consisted of 81% MCC, 14.2% CMC 7LF, and 4.8% CMC 12M31P.

Activation of the produced powder in deionized water at room temperature at 2.6% solids demonstrated an initial viscosity of 2250 cps and a set-up (24 hrs) viscosity of 6700 cps. The 2.6% solids dispersion was measured after 24 hrs set-up with a Texas Instruments Rheometer and exhibited a set-up gel strength G' of 68 Pa. The colloidal content was 89.2%.

Comparative Example 1a

Co-extruded MCC Wetcake:7LF CMC:12M31P CMC

First, 81% MCC wetcake, 14.2% CMC 7LF, and 4.8% CMC 12M31P, were co-extruded. The extrudate was slippery, caused by the content of high DS CMC 12M31P. The extrusion did not generate sufficient work profile. The extrudate was then redispersed in water, homogenized, and spray-dried into powder.

Activation of the powder in deionized water at room temperature at 2.6% solids demonstrated an initial viscosity of 140 cps and a set-up viscosity of 1800 cps. The 2.6% solids dispersion was measured after 24 hrs set-up with a Texas Instruments Rheometer and exhibited a very low set-up gel strength G' of 6 Pa. The colloidal content was only 59.8%.

Comparative Example 1b

Dry Blended Powder of MCC:CMC 7LF Product with 12M31P CMC Powder

Dry powder of commercial colloidal product (85% MCC: 15% CMC 7LF) was dry-blended with 5% by weight CMC 12M31P (Ashland) powder (based on the total weight of MCC:CMC 7LF). The combined powders were activated at 2.6% solids by dispersion in deionized water. This system consisted of 81% MCC, 14.2% CMC7LF, and 4.8% CMC 12M31. It had an initial viscosity at room temperature of 380 cps, a set-up (24 hrs) viscosity of 2300, and a very low set-up gel strength G' of 8 Pa. The colloidal content was 67.7%.

Example 2

Co-Extruded 90% MCC:10% 7LF CMC, then blended in 4.8% 12M31P CMC

First, 90% MCC wetcake was co-extruded with 10% CMC 7LF (Ashland). Then the MCC:CMC 7LF extrudate was dispersed in water and blended with 5% wt 12M31P CMC (Ashland) based on the total weight of MCC:CMC 7LF. Thereafter, the blended system was homogenized, and spray-dried into powder. The final powder consisted of 85.7% MCC, 9.5% CMC 7LF, and 4.8% CMC 12M31P.

Activation of the powder in deionized water at room temperature at 2.6% solids demonstrated an initial viscosity of 2150 cps, a set-up viscosity of 4600 cps, and set-up gel strength G' of 65 Pa The colloidal content was 89.3%.

Example 2a

Co-Extruded 85.7% MCC:9.5% 7LF CMC: 4.8% 12M31P CMC

Three components, 85.7% MCC wetcake, 9.5% 7LF CMC, and 4.8% 12M31P CMC, were co-extruded. The extrudant was slippery and did not generate a sufficient work profile. The extrudant was dispersed in water, homogenized, and spray-dried into powder.

Activation of the powder in deionized water at room temperature at 2.6% solids demonstrated an initial viscosity of 200 cps, set-up viscosity after 24 hrs of 1650, and a set-up gel strength G' of 7 Pa. The colloidal content was 53.6%.

Example 3

Co-Extruded (85% MCC/15% CMC 7LF), then Blended in 4.8% 9H7F CMC

First, 85% MCC wetcake was co-extruded with 15% CMC 7LF (Ashland). Then the MCC:CMC 7LF extrudate was dispersed in water and blended with 5% wt 9H7F CMC (Ashland) based on the total weight of MCC:CMC 7LF. Thereafter, the blended system was homogenized, and spray-dried into powder. The final powder consisted of 81% MCC, 14.2% CMC 7LF, and 4.8% CMC 9H7F.

Activation of the produced powder in deionized water at room temperature at 2.6% solids demonstrated an initial viscosity of 5,000 cps, a set-up viscosity of 6400 cps, and a set-up gel strength G' of 30 Pa.

Comparative Example 3a

Co-Extruded MCC with 9H7F CMC

MCC wetcake was co-extruded with 9H7F CMC (Ashland) in an 85:15 weight ratio. The MCC:CMC extrudate was then dispersed, homogenized, and spry-dried into powder.

Activation of the produced powder in deionized water at room temperature at 2.6% solids demonstrated 13,600 cps initial viscosity and 10,000 cps set-up viscosity after 24 hrs. The set-up gel strength G' was 18 Pa.

Example 4

Co-Extruded (85% MCC:15% CMC 7LF), then blended in 4.8% DrisPac CMC

First, 85% MCC wetcake was co-extruded with 15% CMC 7LF (Ashland). Then the MCC:CMC7LF extrudate was dispersed in water and blended with 5% wt DrisPac CMC (Ashland) based on the total weight of MCC:CMC 7LF. Thereafter, the blended system was homogenized and spray-dried into powder. The final powder consisted of 81% MCC, 14.2% CMC 7LF, and 4.8% DrisPac CMC.

Activation of the produced powder in deionized water at room temperature at 2.6% solids demonstrated an initial viscosity of 2,600 cps, and a set-up viscosity of 5250 cps and set-up gel strength G' of 30 Pa.

Example 5

Co-Extruded (88% MCC:6% CMC 7LF:6% CMC 7MF), then Blended in Second CMC

MCC wetcake was co-extruded with 7LF CMC and 7 MF CMC at an 88:6:6 weight ratio. The extrudate was then further extruded by one more pass at a lab co-rotating twin-screw extruder.

Case 5A)—Comparative Sample. The final extrudant was redispersed in deionized water and spray-dried into powder. It had an initial viscosity of 3700 cps when dispersed in water at 2.65 solids and a set-up viscosity after 24 hrs of 7000 cps. The G' was 70 Pa. This product was dispersed in water at very gentle shear, and the ease of water dispersion of this product was used as reference for the other products below in this example.

Case 5B)—Inventive Sample. The final extrudant was dispersed in deionized water where 5% high DS CMC Aqualon 12M31P (based on the weight of the total extrudate) had already been dissolved. This combination was then spray-dried into powder. It had an initial viscosity of 4300 cps when dispersed in water at 2.6% solids and a set-up viscosity of 6100 cps after 24 hrs. The G' was 90 Pa. This product, when stirred under gentle shear, dispersed fast and easily as compared to Case 5A, as seen by visual observation.

Case 5C)—Inventive Sample. The final extrudant was dispersed in deionized water where 10% high DS CMC Aqualon 12M31P (based on the weight of the total extrudate) had already been dissolved. This combination was then spray-dried into powder. It had an initial viscosity of 4400 cps when dispersed in water at 2.6% solids and a set-up viscosity of 7400 cps after 24 hrs. The G' was 92 Pa. This product, when stirred under gentle shear, dispersed fast and easily as compared to Case 5A, by visual observation.

Case 5D)—Comparative Sample. The final extrudate was dispersed in deionized water where 5% low viscosity-low DS CMC Aqualon 7LF (based on the weight of the total extrudate) had already been dissolved. This combination was then spray-dried into powder. It had an initial viscosity of 3050 cps when dispersed in water at 2.6% solids and a set-up viscosity of 7400 cps after 24 hrs. The G' was 60 Pa. This product, when stirred under gentle shear, dispersed fast and easily as compared to Case 5A, but not as good as Case 5B and 5C where high DS CMC were used, as seen by visual observation.

Example 6

Co-Extruded (85% MCC:15% CMC 7LF), then Blended in Tamarind Seed Gum

MCC wetcake was co-extruded with 7LF CMC, at an 85:15 weight ratio. The extrudate was then redispersed in deionized water, blended with 15% by weight of Tamarind seed gum. The system was then homogenized and spray-dried into powder.

Activation of the powder in deionized water at room temperature at 2.6% solids demonstrated an initial viscosity of 1100 cps, a set-up viscosity of 4275 cps, and a set-up gel strength G' of 50 Pa.

Food Applications (FA):

Example FA1: 40° Brix and 50° Brix Bake Stable Fruit Filling Based on Concentrate Raspberry Samples were prepared using A) a dose range of Avicel®RC591 colloidal MCC made at FMC as described in Comparative Material 1; and B) a dose range of high gel viscosity colloidal MCC by the instant invention as described in Example 1.

| 40° Brix Case Formulation | Sample A % by wt | Sample B % by wt |
| --- | --- | --- |
| Glucose syrup 60 DE | 25 | 25 |
| Sugar | 10 | 10 |
| 65° Brix concentrate raspberry | 9 | 9 |
| Modified Starch | 3.5 | 3.5 |
| Tri sodium citrate powder | 0.15 | 0.15 |
| 50% solution of anhydrate citric acid | 0.1 | 0.1 |
| AVICEL ® RC 591 colloidal MCC | 0 to 1.5 | — |
| High gel viscosity colloidal MCC, (Invention embodiment) | — | 0 to 1.5 |
| Water | to 100 | to 100 |

| 50° Brix Case Formulation | Sample A % by wt | Sample B % by wt |
| --- | --- | --- |
| Glucose syrup 60 DE | 25 | 25 |
| Sugar | 20 | 20 |
| 65° Brix concentrate raspberry | 9s | 9 |
| Modified Starch | 3.5 | 3.5 |
| Tri sodium citrate powder | 0.15 | 0.15 |
| 50% solution of anhydrate citric acid | 0.1 | 0.1 |
| AVICEL ® RC 591 Colloidal MCC | 0 to 1.5 | — |
| High gel viscosity colloidal MCC, (Invention embodiment) | — | 0 to 1.5 |
| Water | to 100 | to 100 |

Process:

The colloidal MCC, the other dry powders, and the water were weighed out separately. The colloidal MCC was first dispersed in water with a high shear mixing for 10 minutes using a Silverson mixer. Then the glucose syrup was preheated at 40° C. and added with the other dry powders in the previous mixture. Then the product was heated to 90° C. in a water bath while gently mixing. The fruit concentrate was then added and mixed until smooth. Finally, the citric acid was added and mixed until smooth and the product was hot filled in appropriate containers.

Bake Stability Test:

Bake stability was determined by measuring shape retention. Shape retention is defined as the capacity of a fruit filling preparation to retain its initial shape and volume after being baked for a definite amount of time at a given temperature. The bakery oven was preheated to 200° C.

Cups (30 ml) cups were filled with sample product. The fillings from the 30 ml cups were deposited in the middle of concentric circles on a paper sheet on a bakery sheet on the oven plate. The plate was positioned in the middle of the oven. The spread of the material on the 16 axes of the 5 concentric circles was recorded before and after baking. Fillings were baked at 200° C. for 10 minutes. The averages of the material spread were calculated (i.e., Av before and Av after baking) as percentages.

Evaluation of the Samples: Results of bake stability are described in Tables FA1.1 and FA1.2.

|  | Use Levels % | | | |
| --- | --- | --- | --- | --- |
| % Spread in 40° Brix Case | 0% | 0.5% | 1.0% | 1.5% |
| Sample A (RC591) | 48.8 | 31.12 | 14.78 | 6.87 |
| Sample B (invention) | 48.8 | 21.12 | 6.1 | 3.52 |

TABLE FA1.2

|  | Use Levels % | | | |
| --- | --- | --- | --- | --- |
| % Spread in 50° Brix Case | 0% | 0.5% | 1.2% | 1.5% |
| Sample A (RC591) | 48.8 | 31.5 | 31.5 | 22.8 |
| Sample B (invention) | 48.8 | Not tested | 7.29 | Not tested |

CONCLUSION

Sample B (the present invention) showed good to excellent bake stability (i.e., low spread in %).

What is claimed is:

1. A process for a making a stabilizer composition comprising:
   a) blending a microcrystalline cellulose wetcake with a first carboxymethyl cellulose having a DS of 0.45-0.85 in an amount of 5% to 25% by weight of the total composition;
   b) extruding the product of step a);
   c) either
      i) blending and subsequently extruding a second carboxymethyl cellulose having a DS of 0.9-1.5 in an amount of 2% to 20% by weight of the total composition, into the product of step b); or
      ii) preparing a water dispersion comprising the microcrystalline cellulose:carboxymethylcellulose extrudate of step b) and a second carboxymethyl cellulose having a DS of 0.9-1.5, wherein the second carboxymethyl cellulose is present in an amount of 2% to 20% by weight of the total composition; and
   d) drying the product of step c);
   wherein the stabilizer composition has an initial viscosity of at least 750 cps, a set-up viscosity of at least 3200 cps, and a set-up gel strength G' of at least 20 Pa when dispersed in water at 2.6% solids concentration.

2. The process of claim 1 wherein step c) the second carboxymethylcellulose is in an amount of 4% to 8% by weight of the total composition.

3. The process of claim 1 wherein the first carboxymethyl cellulose is sodium carboxymethyl cellulose having a DS of about 0.7 and the second carboxymethyl cellulose is sodium carboxymethyl cellulose having a DS of about 1.2.

4. The process of claim 1 wherein the drying step d) is spray drying, fluidized bed drying, flash drying, or bulk drying.

* * * * *